United States Patent [19]
Thompson

[11] Patent Number: 6,132,460
[45] Date of Patent: Oct. 17, 2000

[54] STENT

[75] Inventor: Paul J. Thompson, New Hope, Minn.

[73] Assignee: Intratherapeutics, Inc., St. Paul, Minn.

[21] Appl. No.: 09/049,486

[22] Filed: Mar. 27, 1998

[51] Int. Cl.$^7$ ........................................ A61F 2/00
[52] U.S. Cl. ................................................. 623/1.15
[58] Field of Search ............................ 623/1, 11, 12, 623/1.15

[56]  References Cited

U.S. PATENT DOCUMENTS

| | | | |
|---|---|---|---|
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 5,019,085 | 5/1991 | Hillstead | 606/108 |
| 5,195,984 | 3/1993 | Schatz | 606/195 |
| 5,342,348 | 8/1994 | Kaplan | 604/891.1 |
| 5,419,760 | 5/1995 | Narciso, Jr. | 604/8 |
| 5,421,955 | 6/1995 | Lau et al. | 216/48 |
| 5,443,500 | 8/1995 | Sigwart . | |
| 5,449,373 | 9/1995 | Pinchasik et al. | 606/198 |
| 5,476,508 | 12/1995 | Amstrup . | |
| 5,514,154 | 5/1996 | Lau et al. | 606/195 |
| 5,540,712 | 7/1996 | Kleshinski et al. | 606/198 |
| 5,569,295 | 10/1996 | Lam . | |
| 5,591,197 | 1/1997 | Orth et al. . | |
| 5,649,977 | 7/1997 | Campbell . | |
| 5,695,516 | 12/1997 | Fischell et al. | 606/194 |
| 5,697,971 | 12/1997 | Fischell et al. | 623/1 |
| 5,707,386 | 1/1998 | Schnepp-Pesch et al. . | |
| 5,707,387 | 1/1998 | Wijay . | |
| 5,718,713 | 2/1998 | Frantzen . | |
| 5,725,572 | 3/1998 | Lam et al. . | |
| 5,728,131 | 3/1998 | Frantzen et al. . | |
| 5,741,327 | 4/1998 | Frantzen . | |
| 5,800,526 | 9/1998 | Anderson et al. . | |
| 5,810,872 | 9/1998 | Kanesaka et al. . | |
| 5,853,419 | 12/1998 | Imran . | |
| 5,888,201 | 3/1999 | Stinson et al. . | |
| 5,928,280 | 7/1999 | Hansen et al. . | |

FOREIGN PATENT DOCUMENTS

| | | |
|---|---|---|
| 0 709 067 A2 | 5/1996 | European Pat. Off. . |
| 0 732 088 A2 | 9/1996 | European Pat. Off. . |
| 0 800 800 A1 | 10/1997 | European Pat. Off. . |
| 2 764 794 | 12/1998 | France . |
| 197 22 384 A1 | 12/1998 | Germany . |

OTHER PUBLICATIONS

Dunitz, M., Excerpts from "Handbook of Coronary Stents," Rotterdam Thoraxcentre Group, University Hospital Dijkzigt, Rotterdam, The Netherlands, 1997 (23 pages).

*Primary Examiner*—Michael J. Milano
*Attorney, Agent, or Firm*—Merchant & Gould P.C.

[57]  ABSTRACT

The present disclosure relates to an intraluminal stent including a reticulated tube having an un-deployed diameter and expandable to an enlarged diameter. When the tube is at the un-deployed diameter, the tube has cell-defining portions with opposing surfaces defining an open cell bounded by the cell-defining portions. The cell has a major axis and a minor axis. The cell-defining portions include first and second longitudinal segments each having a longitudinal axis extending parallel to and positioned on opposite sides of the cell major axis. The longitudinal segments have an undulating pattern to define a plurality of peaks and valleys spaced outwardly and inwardly, respectively, from the longitudinal axes. The first and second longitudinal segments are interconnected at opposite ends.

16 Claims, 7 Drawing Sheets

STENT

I. BACKGROUND OF THE INVENTION

1. Field of the Invention

This invention pertains to stents for use in intraluminal applications. More particularly, this invention pertains to a novel structure for such stents.

2. Description of the Prior Art

Stents are widely used for numerous applications where the stent is placed in the lumen of a patient and expanded. Such stents may be used in coronary or other vasculature, as well as other body lumens.

Commonly, stents are cylindrical members. The stents expand from reduced diameters to enlarged diameters. Frequently, such stents are placed on a balloon catheter with the stent in the reduced-diameter state. So placed, the stent is advanced on the catheter to a placement site. At the site, the balloon is inflated to expand the stent to the enlarged diameter. The balloon is deflated and removed, leaving the enlarged diameter stent in place. So used, such stents are used to expand occluded sites within a patient's vasculature or other lumen.

Examples of prior art stents are numerous. For example, U.S. Pat. No. 5,449,373 to Pinchasik et al. teaches a stent with at least two rigid segments joined by a flexible connector. U.S. Pat. No. 5,695,516 to Fischell teaches a stent with a cell having a butterfly shape when the stent is in a reduced-diameter state. Upon expansion of the stent, the cell assumes a hexagonal shape.

In stent design, it is desirable for the stent to be flexible along its longitudinal axis to permit passage of the stent through arcuate segments of a patient's vasculature or other body lumen. Preferably, the stent will have at most minimal longitudinal shrinkage when expanded and will resist compressive forces once expanded.

II. SUMMARY OF THE INVENTION

According to a preferred embodiment of the present invention, an intraluminal stent is disclosed comprising a reticulated tube having a rest or un-deployed diameter and expandable to an enlarged diameter. When the tube is at the rest diameter, the tube has cell-defining portions with opposing surfaces defining an open cell bounded by the cell-defining portions. The cell has a major axis and a minor axis. The cell-defining portions include first and second longitudinal segments each having a longitudinal axis extending parallel to and positioned on opposite sides of the cell major axis. The longitudinal segments have an undulating pattern to define a plurality of peaks and valleys spaced outwardly and inwardly, respectively, from the longitudinal axes. The first and second longitudinal segments are interconnected at opposite ends.

III. BRIEF DESCRIPTION OF THE DRAWINGS

IV. DESCRIPTION OF THE PREFERRED EMBODIMENT

Referring now to the several drawing figures in which identical elements are numbered identically, a description of the preferred embodiment of the present invention will now be provided. Where several embodiments are shown, common elements are similarly numbered and not separately described with the addition of apostrophes to distinguish the embodiments.

Figure 1:
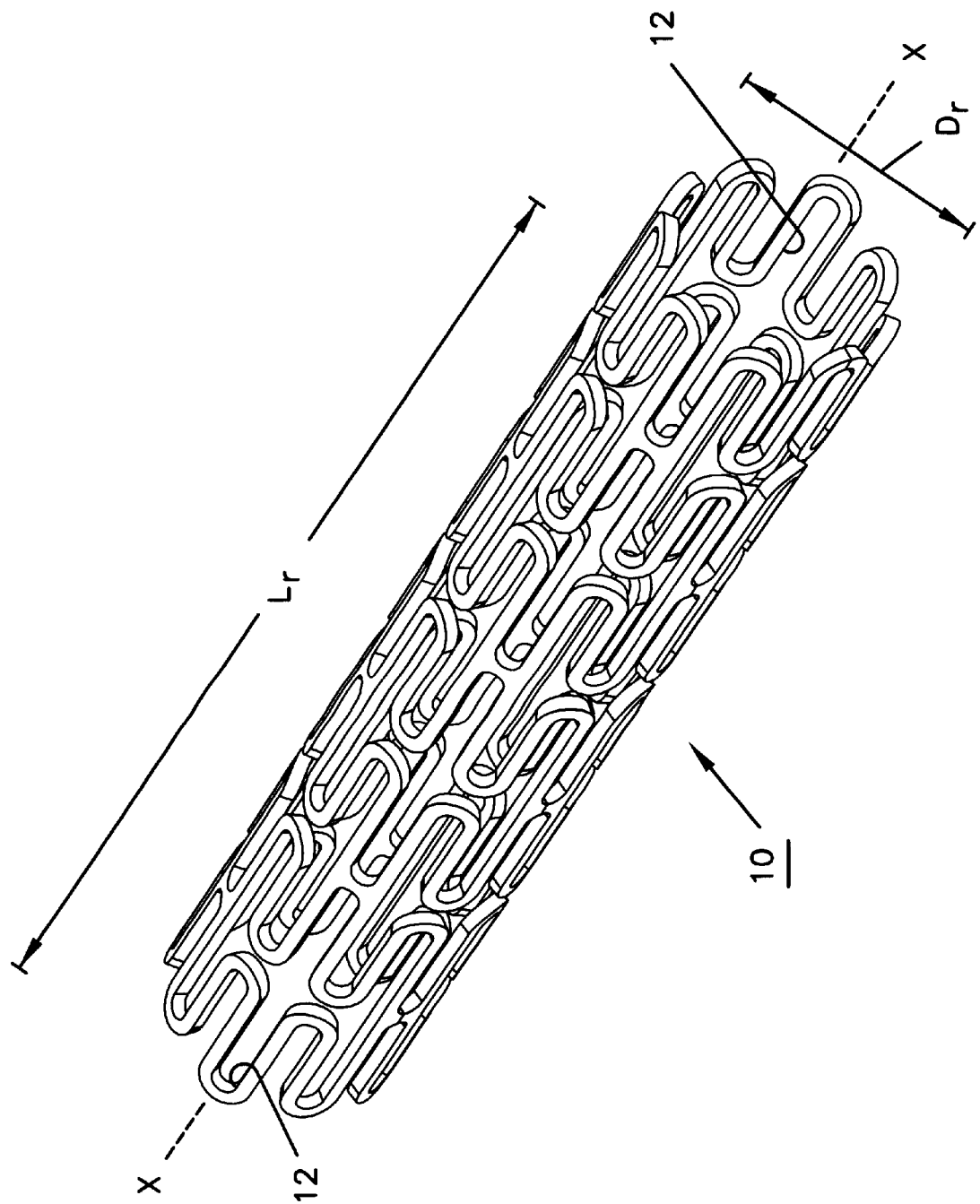
FIG. 1 is a perspective view of a first embodiment of a stent according to the present invention shown in a rest diameter state and showing a plurality of stent cells each having a major axis perpendicular to an axis of the stent.
Figure 2:
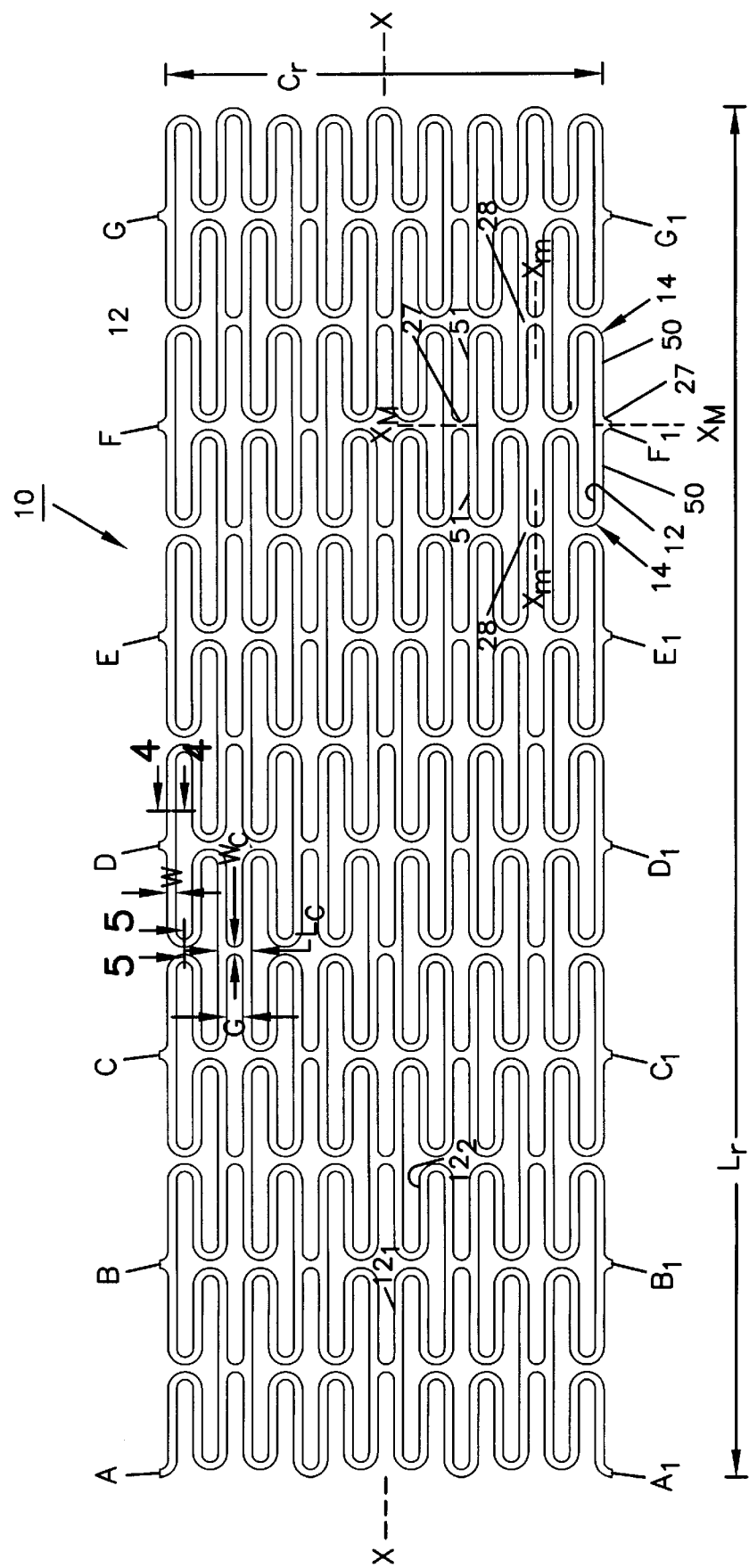
FIG. 2 is a plan view of the stent of FIG. 1 as it would appear if it were longitudinally split and laid out flat.
Figure 6:
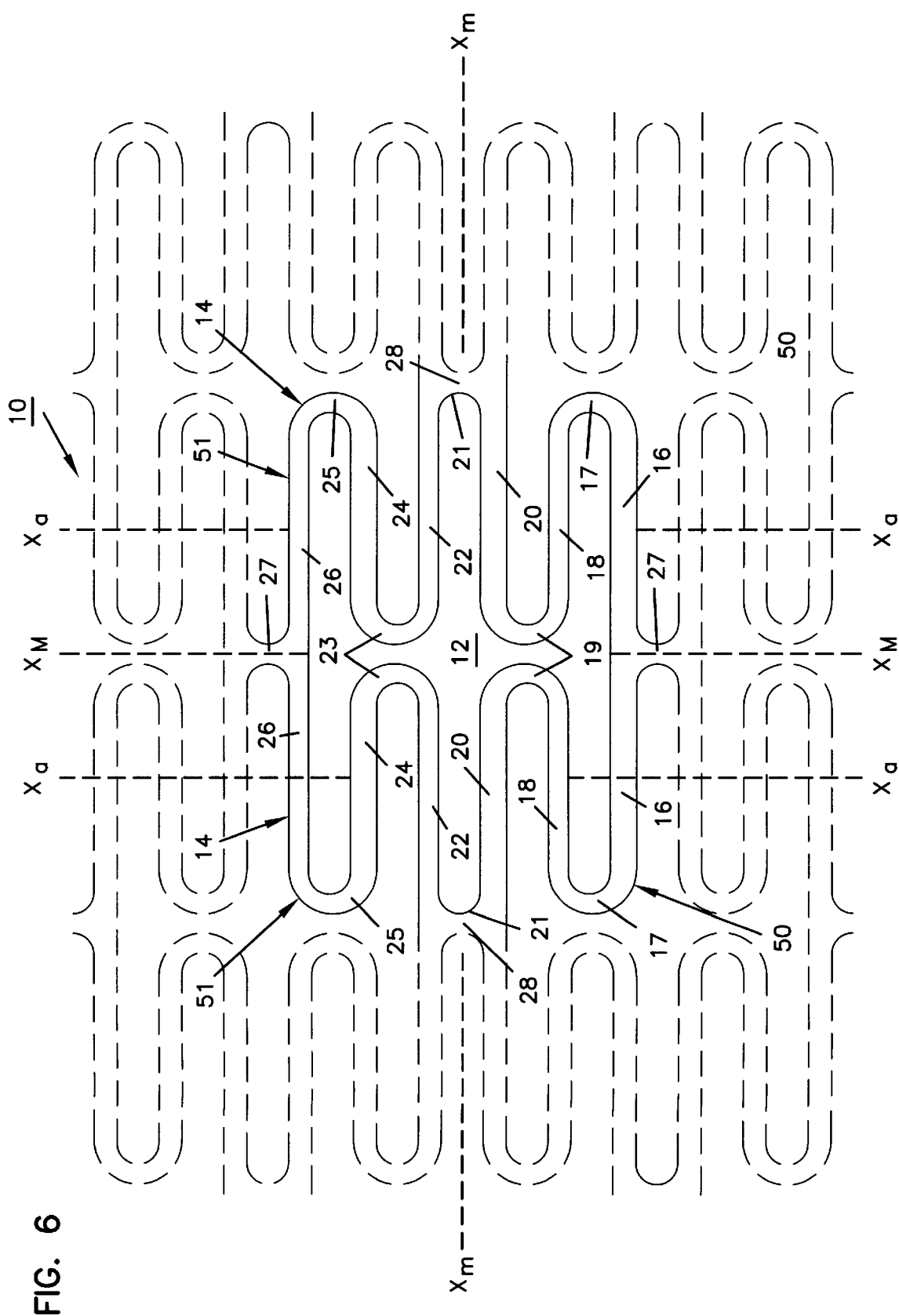
FIG. 6 is an enlarged view of a portion of FIG. 2 illustrating a cell structure with material of the stent surrounding adjacent cells shown in phantom lines.

FIG. 1 illustrates a stent 10 having a rest length $L_r$ and an un-deployed or reduced diameter $D_r$. For ease of illustration, the stent 10 is shown flat in FIG. 2 which illustrates a rest circumference $C_r$ ($C_r = \pi D_r$). In FIG. 2, locations A, B, C, D, E, F and G are shown severed from their normally integrally formed locations $A_1$, $B_1$, $C_1$, $D_1$, $E_1$, $F_1$ and $G_1$. This permits the stent 10 to be shown as if it were severed at normally integrally formed locations A–$A_1$, B–$B_1$, C–$C_1$, D–$D_1$, E–$E_1$, F–$F_1$ and G–$G_1$ and laid flat. FIG. 6 is an enlarged portion of the view of FIG. 2 to better illustrate a novel cell structure as will be described.

Figure 3:
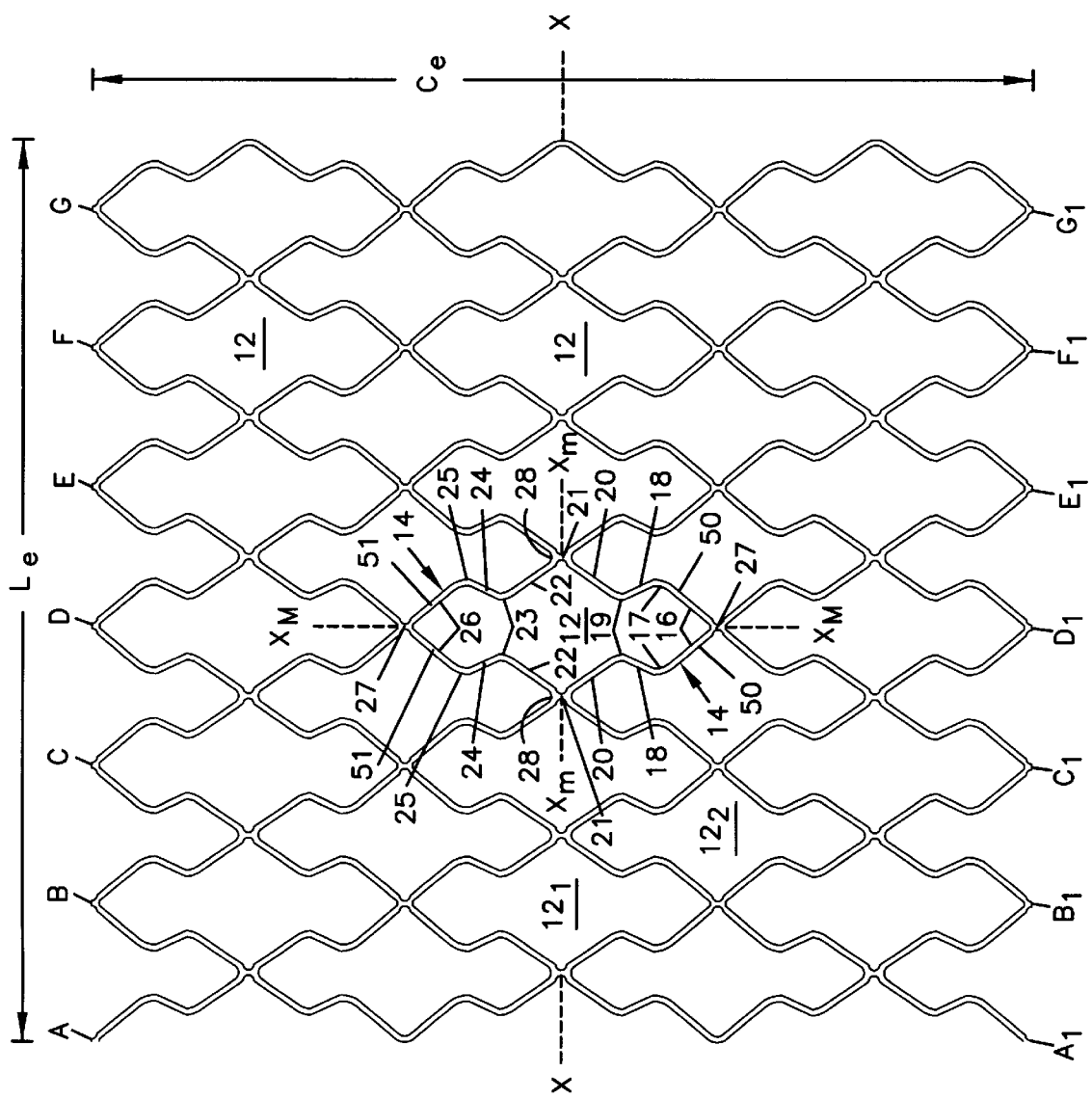
FIG. 3 is the view of FIG. 2 following expansion of the stent to an enlarged diameter.

The stent 10 is a reticulated, hollow tube. The stent 10 may be expanded from the rest diameter $D_r$ (and corresponding rest circumference $C_r$) to an expanded or enlarged diameter. FIG. 3 is a view similar to FIG. 2 (i.e., illustrating the expanded stent 10 as it would appear if longitudinally split and laid flat). Since FIG. 3 is a two-dimensional representation, the enlarged diameter is not shown. However, the enlarged circumference $C_e$ is shown as well as a length $L_e$ following expansion. The expanded diameter is equal to $C_e/\pi$.

As will be discussed length $L_e$ is preferably not more than minimally smaller (e.g., less than 10% smaller) than length $L_r$. Ideally, $L_e$ equals $L_r$.

The material of the stent 10 defines a plurality of cells 12. The cells 12 are bounded areas which are open (i.e., extend through the wall thickness of the stent 10). The stent 10 may be formed through any suitable means including laser or chemical milling. In such processes, a hollow cylindrical tube is milled to remove material and form the open cells 12.

Figure 8:
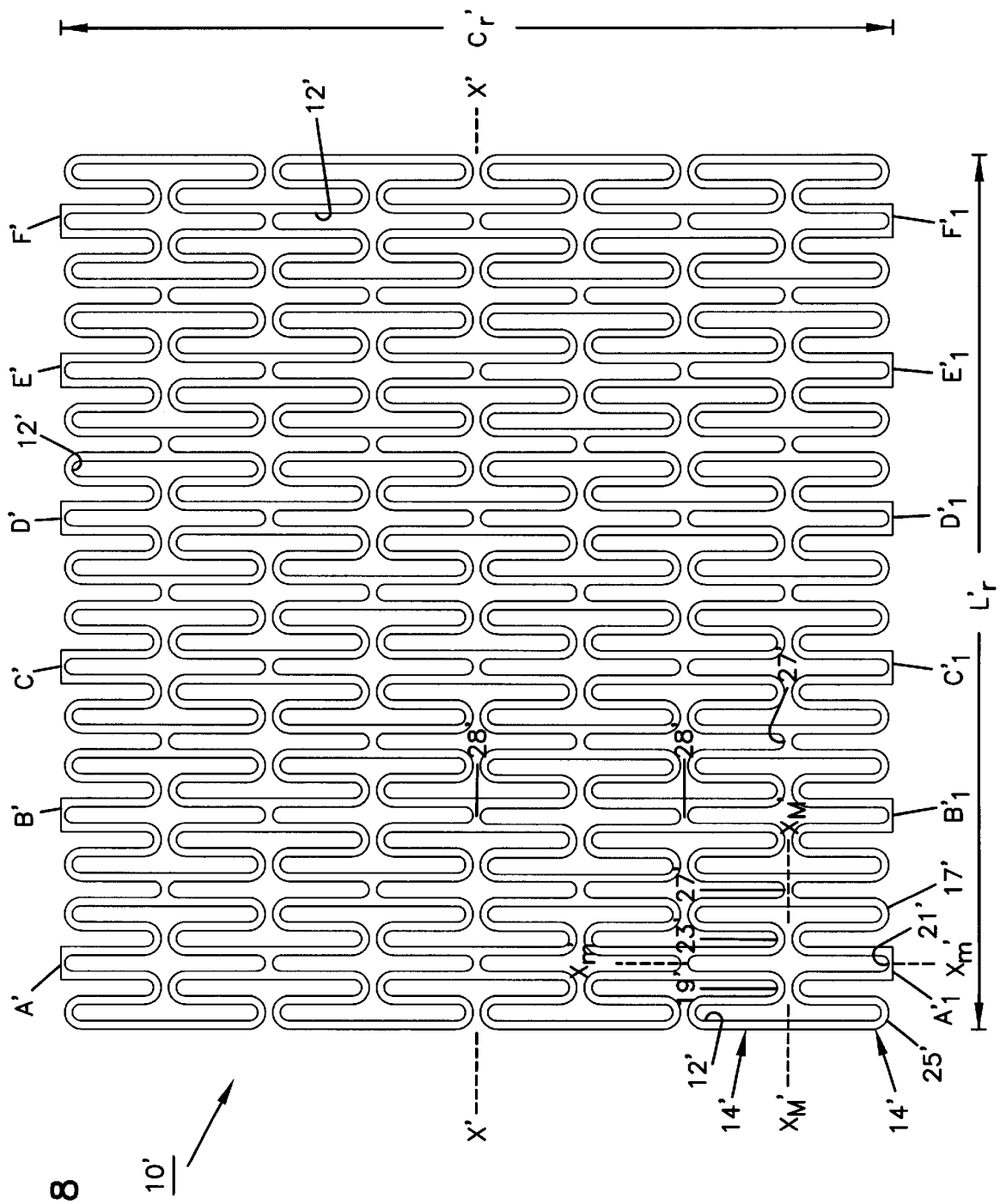
FIG. 8 is the view of FIG. 2 showing an alternative embodiment of the present invention with a major axis of the cell being parallel to an axis of the stent.
Figure 9:
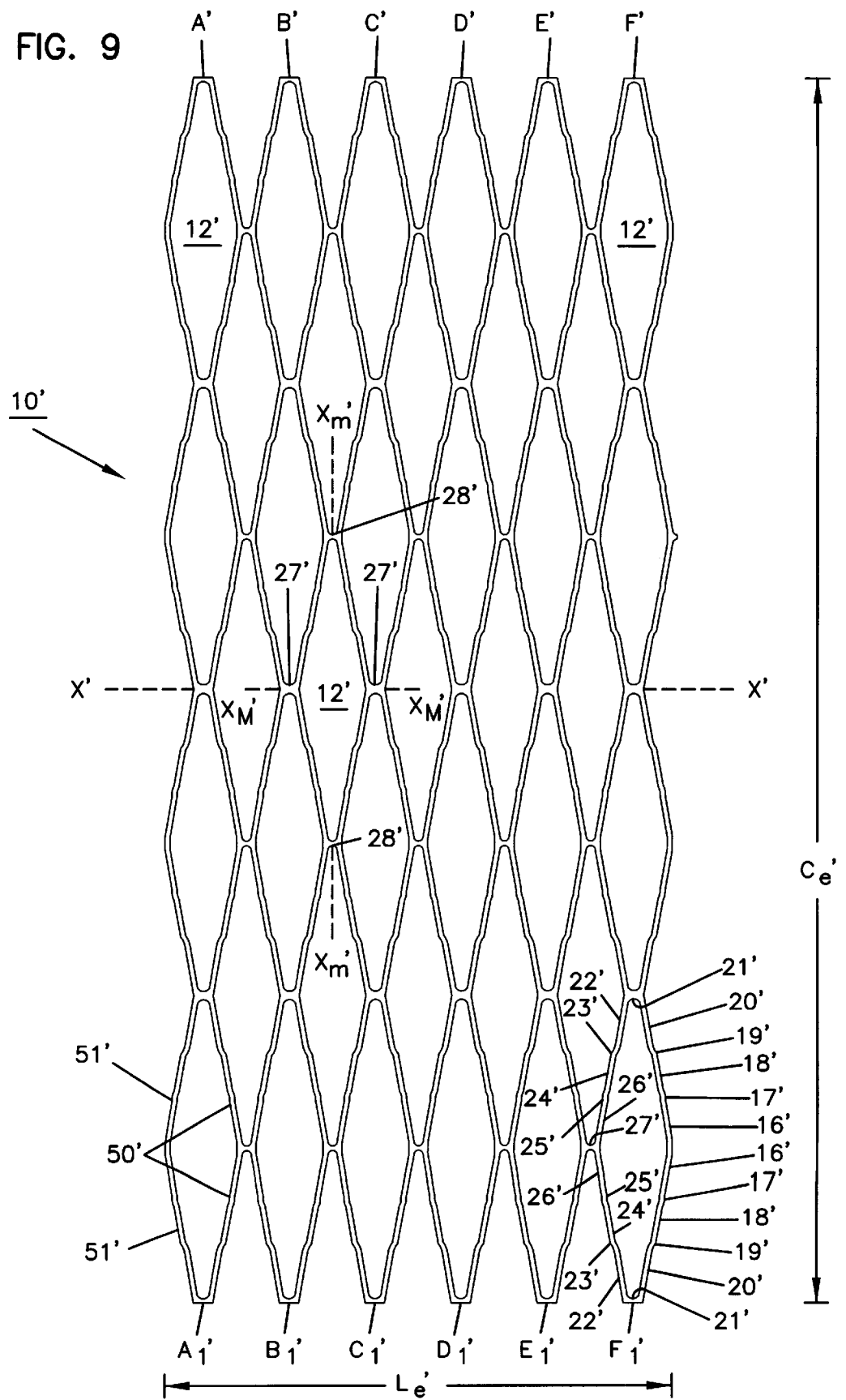
FIG. 9 is the view of FIG. 8 following expansion of the stent to an enlarged diameter.

The cells 12 have a longitudinal or major axis $X_M$—$X_M$ and a transverse or minor axis $X_m$—$X_m$. In the embodiments of FIGS. 1–3, the major axis $X_M$—$X_M$ is perpendicular to the longitudinal cylindrical axis X—X of the stent 10. In the embodiments of FIGS. 8 and 9, the major axis $X_M'$—$X_M'$ is parallel to the longitudinal cylindrical axis X'—X' of the stent 10'. The cell 12 is symmetrical about axes $X_M$—$X_M$ and $X_m$—$X_m$.

The cell 12 is defined by portions of the tube material including first and second longitudinal segments 14. The segments 14 each have a longitudinal axis $X_a$—$X_a$ as shown in FIG. 6. The segments' longitudinal axes $X_a$—$X_a$ are parallel to and positioned on opposite sides of the cell major axis $X_M$—$X_M$.

Each of longitudinal segments 14 has an undulating pattern to define a plurality of peaks 17, 21, 25 and valleys 19, 23. The peaks 17, 21, 25 are spaced outwardly from the longitudinal axes $X_a$—$X_a$ and the valleys 19, 23 are spaced inwardly from the longitudinal axes $X_a$—$X_a$. As used in this context, "inward" and "outward" mean toward and away from, respectively, the cell's major axis $X_M$—$X_M$.

Each of the peaks 17, 21, 25 and valleys 19, 23 is a generally semi-circular arcuate segment. The peaks 17, 21, 25 and valleys 19, 23 are joined by parallel and spaced-apart straight segments 16, 18, 20, 22, 24 and 26 which extend perpendicular to the major axis $X_M$—$X_M$. Linearly aligned straight end portions 16, 26 of opposing segments 14 are joined at first and second longitudinal connection locations 27 spaced apart on the major axis $X_M$—$X_M$. First and second transverse connection locations 28 are spaced apart on the minor axis $X_m$—$X_m$. The first and second transverse connection locations 28 are positioned at the apices of the center peaks 21 of the longitudinal segments 14.

Figure 4:
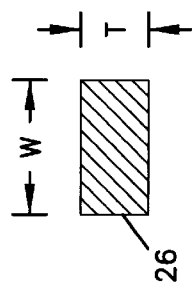
FIG. 4 is a view taken along line 4—4 in FIG. 2.

Except as will be described, the segments 14 have uniform cross-sectional dimensions throughout their length as illustrated in FIG. 4. By way of non-limiting example, the width W and thickness T of the straight line segments 16, 18, 20, 22, 24 and 26 are about 0.0065 inch (about 0.16 mm) and about 0.0057 inch (about 0.14 mm), respectively.

Figure 5:
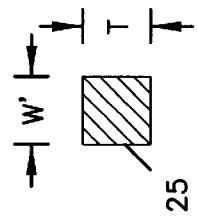
FIG. 5 is a view taken along line 5—5 in FIG. 2.

For reasons that will be described, the width W' (FIG. 5) at the apices of the peaks 17, 21, 25 and valleys 19, 23 is narrower than width W (in the example given, narrow width W' is about 0.0055 inch or about 0.13 mm). The width of the peaks 17, 21, 25 and valleys 19, 23 gradually increases from width W' at the apices to width W at the straight segments 16, 18, 20, 22, 24 and 26. At the longitudinal and transverse connection locations 27, 28, the width $W_C$ (shown in FIG. 2) is preferably equal to or less than the common width W. As shown in FIG. 2, each of the longitudinal and transverse connection locations 27, 28 has a longitudinal length $L_c$ that is greater than two times as long as the common width W. For example, each length $L_c$ is shown as being equal to two times the common width W plus the distance defined by a spacing gap G formed between parallel portions of the undulating pattern.

The combined lengths of segments 16–20 to the apex of peak 21 represent a path length 50 from longitudinal connection location 27 to transverse connection location 28. Similarly the combined lengths of the other arcuate and straight segments 22—26 to the apex of peak 21 represent identical length path lengths 51 of identical geometry from longitudinal connection locations 27 to transverse connection locations 28. Each of the path lengths 50, 51 is longer than a straight-line distance between the transverse and longitudinal connection locations 27, 28. As will be described, the straight-line distance between the transverse and longitudinal connection locations 27, 28 increases as the diameter of the stent 10 is expanded. The path lengths 50, 51 are sized to be not less than the expanded straight-line distance.

The stent 10 includes a plurality of identical cells 12. Opposite edges of the segments 14 define obliquely adjacent cells (such as cells $12_1$, $12_2$ in FIG. 2). Cells 12 having major axes $X_M$—$X_M$ collinear with the major axis $X_M$—$X_M$ of cell 12 are interconnected at the longitudinal connection locations 27. Cells having minor axes collinear with the minor axis $X_m$—$X_m$ of cell 12 are interconnected at the transverse connection locations 28.

As mentioned, the stent 10 in the reduced diameter of FIG. 1 is advanced to a site in a lumen. The stent 10 is then expanded at the site. The stent 10 may be expanded through any conventional means. For example, the stent 10 in the reduced diameter may be placed on the balloon tip of a catheter. At the site, the balloon is expanded to generate radial forces on the interior of the stent 10. The radial forces urge the stent 10 to radially expand without appreciable longitudinal expansion or contraction. Plastic deformation of the material of the stent 10 (e.g., stainless steel) results in the stent 10 retaining the expanded shape following subsequent deflation of the balloon. Alternatively, the stent 10 may be formed of a super-elastic or shape memory material (such as nitinol—a well-known stent material which is an alloy of nickel and titanium).

As the stent 10 expands, the path lengths 50, 51 straighten to accommodate the expansion. FIG. 3 illustrates the straightening of the path lengths 50, 51. In FIG. 3, the stent 10 has been only partially expanded to an expanded diameter less than a maximum expanded diameter. At a maximum expanded size, the path lengths 50, 51 are fully straight. Further expansion of the stent 10 beyond the maximum expanded size would result in narrowing of the minor axis $X_m$—$X_m$ (i.e., a narrowing of a separation between the transverse connection locations and a resulting narrowing of the length $L_r$ of the stent) or would require stretching and thinning of the stent material.

As shown in FIG. 3, during expansion of the stent 10, the straight segments 16, 18, 20, 22, 24 and 26 are substantially unchanged. The straightening of the path lengths 50, 51 results in bending of the arcuate peaks 17, 21, 25 and valleys 19, 23. Since the width W' of the peaks 17, 21, 25 and valleys 19, 23 is less than the width W of the straight segments 16, 18, 20, 22, 24 and 26, the arcuate peaks 17, 21, 25 and valleys 19, 23 are less stiff than the straight segments 16, 18, 20, 22, 24 and 26 and, therefore, more likely to deform during expansion.

As the stent 10 expands, the cells 12 assume a diamond shape shown in FIG. 3. Since the expansion forces are radial, the length of the major axis $X_M$—$X_M$ (i.e., the distance between the longitudinal connection locations 27) increases. The length of the minor axis $X_m$—$X_m$ (and hence the length of the stent 10) remains unchanged.

The stent 10 is highly flexible. To advance to a site, the axis X-X of the stent 10 must bend to navigate through a curved lumen. Further, for placement at a curved site in a lumen, the stent 10 must be sufficiently flexible to retain a curved shape following expansion and to bend as the lumen bends over time. The stent 10, as described above, achieves these objections.

When bending on its axis X—X, the stent 10 tends to axially compress on the inside of the bend and axially expand on the outside of the bend. The present design permits such axial expansion and contraction. The novel cell geometry 12 results in an accordion-like structure which is highly flexible before and after radial expansion. Further, the diamond shape of the cells 12 after radial expansion resists constricting forces otherwise tending to collapse the stent 10.

Numerous modifications are possible. For example the stent 10 may be lined with either an inner or outer sleeve (such as polyester fabric or ePTFE) for tissue growth. Also, the stent may be coated with radiopaque coatings such as platinum, gold, tungsten or tantalum. In addition to materials previously discussed, the stent may be formed of any one of a wide variety of previous known materials including, without limitation, MP35N, tantalum, platinum, gold, Elgiloy and Phynox.

Figure 7:
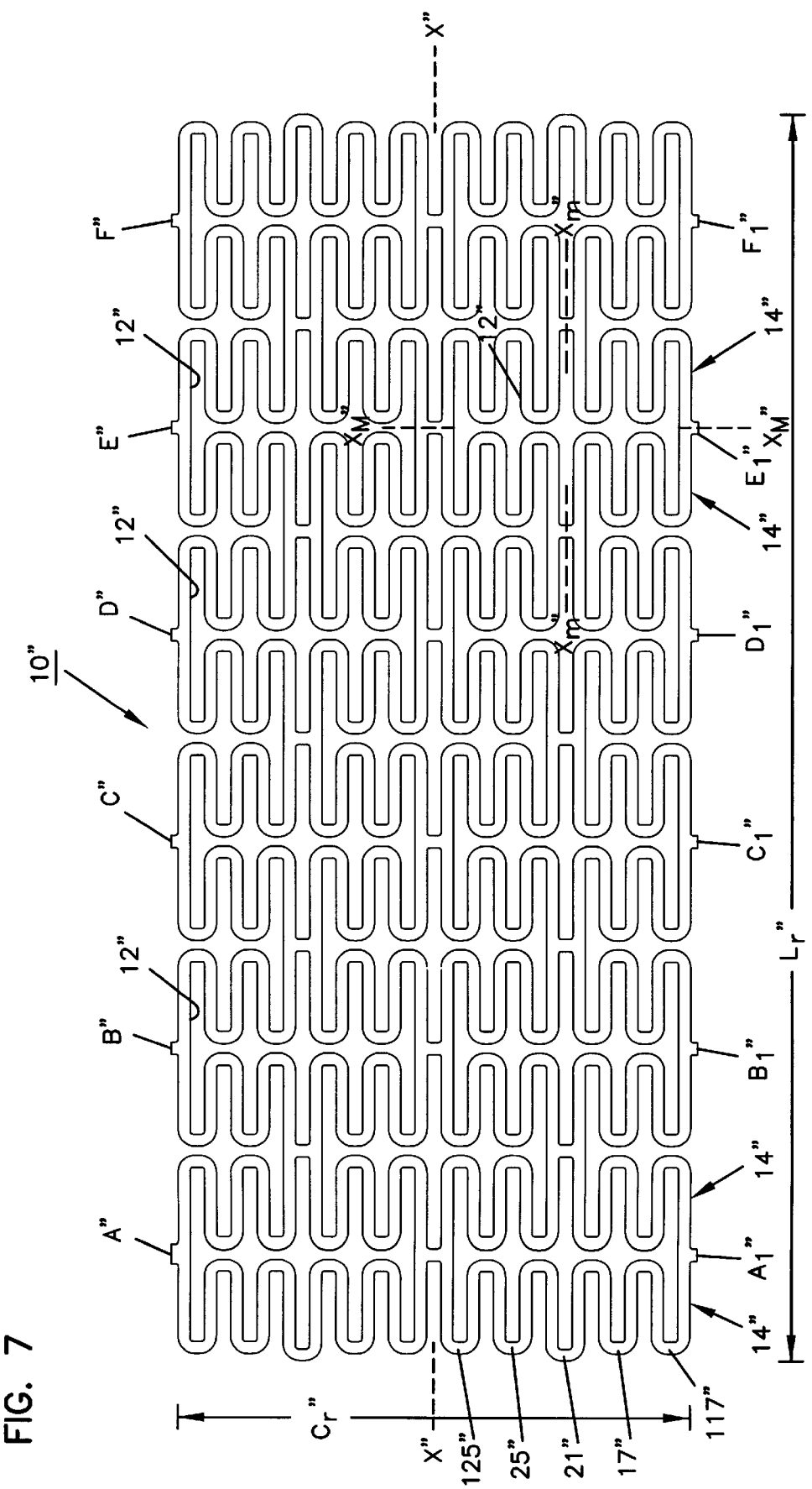
FIG. 7 is the view of FIG. 2 showing an alternative embodiment of the present invention with a cell having five peaks per longitudinal segment.

While three cells 12 are shown in FIG. 2 longitudinally connected surrounding the circumference $C_r$ of the stent, a different number could be so connected to vary the properties of the stent 10 as a designer may elect. Likewise, while each column of cells 12 in FIG. 2 is shown as having three longitudinally connected cells 12, the number of longitudinally connected cells 12 could vary to adjust the properties of the stent. Also, while each longitudinal segment 14 is shown as having three peaks 17, 21, 25 per longitudinal segment 14, the number of peaks could vary. FIG. 7 illustrates a stent 10" with a cell 12" having five peaks 117", 17", 21", 25" and 125" per longitudinal segment 14". Preferably, the longitudinal segment will have an odd number of peaks so that the transverse connection points are at an apex of a center peak.

FIGS. 8 and 9 illustrate an alternative embodiment where the major axis $X_M'$—$X_M'$ of the cells 12' are parallel with the cylindrical axis X'—X' of the stent 10'. In FIG. 9, the expanded stent 10' is shown at a near fully expanded state where the path lengths 50', 51' are substantially linear.

From the foregoing, the present invention has been shown in a preferred embodiment. Modifications and equivalents are intended to be included within the scope of the appended claims.

What is claimed is:

1. A stent comprising:
   a stent body expandable between an un-deployed orientation and a deployed orientation;
   the stent body having cell defining portions with opposing surfaces defining an open cell bounded by the cell defining portions, the cell having a major axis and a minor axis;
   the cell defining portions including first and second longitudinal segments each of which includes:
   a. a longitudinal axis extending parallel to the cell major axis, the longitudinal axes being positioned on opposite sides of the cell major axis; and
   b. an undulating pattern that defines a plurality of peaks and valleys spaced outwardly and inwardly, respectively, from the longitudinal axes;
   the first and second longitudinal segments being interconnected at opposite ends thereof;
   the stent body further including first and second longitudinal connection locations at interconnection points of the interconnected first and second longitudinal segments for connection of the cell to first and second longitudinally adjacent cells, respectively, and first and second transverse connection locations on the first and second longitudinal segments, respectively, for connection of the cell to first and second transversely adjacent cells, respectively;
   the cell defining portions being symmetrical about both the major axis and the minor axis;
   the first and second longitudinal connection locations being positioned on the major axis, and the first and second transverse connection locations being positioned on the minor axis;
   the longitudinal and transverse connection locations each having a transverse width $W_c$ that is at most equal to as a common width W of each of the longitudinal segments; and
   the longitudinal and transverse connection locations each having a longitudinal length $L_c$ that is greater than two times as long as the common width W of each of the longitudinal segments.

2. The stent of claim 1, wherein the peaks are formed by first portions of the longitudinal segments and the valleys are formed by second portions of the longitudinal segments, and the undulating patterns of the cell include sets of substantially parallel portions that interconnect the peaks and valleys and are generally perpendicular with respect to the cell major axis.

3. The stent of claim 2, wherein the second portions of said first and second longitudinal segments are located outside the longitudinal axes when the stent body is expanded to a fully expanded orientation.

4. The stent of claim 1, wherein the stent body plastically deforms as it is expanded from the un-deployed orientation to the deployed orientation.

5. The stent of claim 2, wherein a spacing gap G is formed between each set of substantially parallel portions, and the longitudinal length $L_c$ is generally equal to two times the common width W plus the spacing gap G.

6. The stent of claim 2, wherein at least some of the peaks and valleys are formed by semi-circular portions.

7. The stent of claim 6, wherein the semi-circular portions have cross-sectional areas that are smaller than cross-sectional areas corresponding to the substantially parallel portions.

8. The stent of claim 7, wherein the semi-circular portions include apices, and the cross-sectional areas of the semi-circular portions decrease as said semi-circular portions extend toward said apices.

9. The stent of claim 1, wherein the major axis is parallel to a stent axis of the stent body.

10. The stent of claim 1, wherein the major axis is perpendicular to a stent axis of the stent body.

11. A stent comprising:
    a stent body expandable between an un-deployed orientation and a deployed orientation;
    the stent body having cell defining portions with opposing surfaces defining an open cell bounded by the cell defining portions, the cell having a major axis and a minor axis;
    the cell defining portions including first and second longitudinal segments each of which includes:
    a. a longitudinal axis extending parallel to the cell major axis, the longitudinal axes being positioned on opposite sides of the cell major axis; and
    b. an undulating pattern that defines a plurality of peaks and valleys spaced outwardly and inwardly, respectively, from the longitudinal axes, the plurality of peaks including a central peak positioned at the minor axis and longitudinally adjacent peaks positioned on opposite sides of the central peak, the undulating pattern of the cell including sets of substantially parallel portions that interconnect the peaks and valleys and are generally perpendicular with respect to the cell major axis, the sets of substantially parallel portions corresponding to the central peak being longer than the sets of substantially parallel portions corresponding to the longitudinally adjacent peaks;
    the first and second longitudinal segments being interconnected at opposite ends thereof;
    the stent body further including first and second longitudinal connection locations at interconnection points of the interconnected first and second longitudinal segments for connection of the cell to first and second longitudinally adjacent cells, respectively, and first and second transverse connection locations on the first and second longitudinal segments, respectively, for connection of the cell to first and second transversely adjacent cells, respectively;

the cell defining portions being symmetrical about both the major axis and the minor axis;

the first and second longitudinal connection locations being positioned on the major axis, and the first and second transverse connection locations being positioned on the minor axis; and the transverse connection locations being formed at the central peaks of the undulating patterns, the central peaks being connected directly to central peaks of the first and second transversely adjacent cells such that no intermediate connection members are provided between the interconnected central peaks.

12. The stent of claim 11, wherein the stent body plastically deforms as it is expanded from the un-deployed orientation to the deployed orientation.

13. The stent of claim 11, wherein at least some of the peaks and valleys are formed by semi-circular portions.

14. The stent of claim 11, wherein each of the longitudinal and transverse connection locations has a transverse width $W_c$ that is at most equal to a common width W of each of the longitudinal segments.

15. The stent of claim 11, wherein each of the longitudinal and transverse connection locations has a longitudinal length $L_c$ that is greater than two times as long as a common width W of each of the longitudinal segments.

16. The stent of claim 15, wherein a spacing gap G is formed between each set of substantially parallel portions, and the longitudinal length $L_c$ is generally equal to two times the common width W plus the spacing gap G.

* * * * *

UNITED STATES PATENT AND TRADEMARK OFFICE
CERTIFICATE OF CORRECTION

PATENT NO.    : 6,132,460
DATED         : October 17, 2000
INVENTOR(S)   : Thompson It is certified that error appears in the above-identified patent and that said Letters Patent is hereby corrected as shown below:

Column 5,
Line 62, "as" should be deleted.

Signed and Sealed this

Fourth Day of June, 2002

Attest:

Attesting Officer

JAMES E. ROGAN
*Director of the United States Patent and Trademark Office*